United States Patent [19]

Lubsen et al.

[11] 4,189,442

[45] Feb. 19, 1980

[54] SEPARATION OF FATTY ACID ESTERS

[75] Inventors: Timothy A. Lubsen, Wyoming, Ohio; Gustav A. Maag, Mitchell, Ky.

[73] Assignee: The Procter & Gamble Company, Cincinnati, Ohio

[21] Appl. No.: 19,691

[22] Filed: Mar. 12, 1979

Related U.S. Application Data

[63] Continuation-in-part of Ser. No. 952,439, Oct. 18, 1978, abandoned.

[51] Int. Cl.$^2$ .............................. C09F 5/10; C11B 3/00
[52] U.S. Cl. ............................... 260/428.5; 560/218; 560/248; 260/426; 260/427
[58] Field of Search .................... 260/428, 428.5, 419, 260/412.8

[56] References Cited

U.S. PATENT DOCUMENTS

| | | | |
|---|---|---|---|
| 2,985,589 | 5/1961 | Broughton et al. | 210/34 |
| 3,510,423 | 5/1970 | Nenzil et al. | 208/310 |
| 4,048,205 | 9/1977 | Nenzil et al. | 260/428 |
| 4,049,688 | 9/1977 | Nenzil et al. | 260/428.5 |

OTHER PUBLICATIONS

JAOCS 40 pp. 513–514 (Oct. 1963).
JAOCS 41 pp. 388–390 (May 1964).
JAOCS 54 pp. 319–321 (Aug. 1977).
JAOCS 55 pp. 561–563 (Jul. 1978).

*Primary Examiner*—John F. Niebling
*Attorney, Agent, or Firm*—Ronald L. Hemingway; Richard C. Witte

[57] ABSTRACT

Fatty acid ester mixture is separated according to degree of unsaturation utilizing particular resin adsorbent and particular solvent.

15 Claims, No Drawings

SEPARATION OF FATTY ACID ESTERS

CROSS REFERENCE TO RELATED APPLICATION

This application is a continuation-in-part of copending application Ser. No. 952,439, filed Oct. 18, 1978, now abandoned.

BACKGROUND OF THE INVENTION

The field of this invention is the separation of fatty acid esters. The separated esters are useful, for example, as chemical intermediates in the manufacture of fatty chemical derivatives.

Fractional distillation is the most common method now being used commercially to separate fatty acid esters. This unit operation separates on the basis of chain length only. It does not separate on the basis of unsaturation.

Fractional solvent crystallization, which is used to separate fatty acids on the basis of unsaturation, is not economic for fatty acid esters. Temperatures of minus 50° F. to minus 70° F. and lower would have to be used, the crystals would be very fragile, and there would be a mutual solubility between unsaturate components; this provides a very expensive process for a substantially incomplete separation.

Urea adduction is another uneconomic process for separating fatty acid esters. This consists, for example, of admixing the esters to be separated with urea and acetone and cooling whereby the urea forms a crystal cage around the highest melting point esters (usually the saturates). Recovery of ester from the adduct is difficult. Moreover, this process is not as effective for separating one unsaturate from another. Furthermore, this process is difficult to adapt to continuous operation.

It is an object of this invention to provide a process for separating fatty acid esters according to degree of unsaturation which does not require low uneconomic temperatures or difficult recovery of product and which can separate one unsaturate from another and which is readily operated on a continuous basis.

BRIEF DESCRIPTION OF THE INVENTION

The above object and other objects and advantages are obtained as follows: The fatty acid ester mixture to be separated according to degree of unsaturation (that is, the feed) is dissolved in particular solvent. The solution which is formed is contacted with particular resin adsorbent, and fatty acid ester of higher degree of unsaturation is selectively adsorbed on such adsorbent, and a fraction of the ester mixture being separated which is enriched (compared to the feed) in content of ester of lesser degree of unsaturation is left in solution in the solvent. Solution in the solvent of the fraction which is enriched in content of ester of lesser degree of unsaturation is removed from contact with the resin which has selectively adsorbed fatty acid ester of higher degree of unsaturation; this solution is denoted a raffinate. Fraction enriched in content of ester of lesser degree of unsaturation can be readily recovered from the raffinate as described later. The resin which has selectively adsorbed thereon fatty acid ester of higher degree of unsaturation is contacted with solvent to cause desorption of adsorbed ester and provide a solution in the solvent of fraction enriched (compared to the feed) in content of ester of higher degree of unsaturation. Solution in solvent of fraction enriched in content of ester of higher degree of unsaturation is removed from contact with the resin which has undergone desorption of ester; this solution is denoted as extract. Fraction enriched in content of ester of higher degree of unsaturation can be readily recovered from the extract as described later. The solvent which is used to dissolve feed for selective adsorption and the solvent which is used to cause desorption have the same composition. In other words, in any particular run, the same solvent composition is present in the step of adsorption, in the step where fraction enriched in content of ester of lesser degree of unsaturation is removed from contact with resin, in the step of desorption and in the step where fraction enriched in content of ester of higher degree of unsaturation is removed from contact with resin.

The solvents useful in the process of the invention generally described above are characterized by solubility parameters ranging from about 7.0 to about 10.5, solubility parameter dispersion components ranging from about 7.0 to about 9.0, solubility parameter polar components ranging from about 0.2 to about 5.1, and solubility parameter hydrogen bonding components ranging from about 0.3 to about 7.4. Solvents which are of moderate polarity do not have the disadvantage of high polarity solvents of attacking the resin adsorbent thereby destroying such adsorbent or shortening its life. The use of the same solvent composition as the dissolving phase during adsorption and as the vehicle for desorption (that is, as the desorbent) enables solvent to be reused without the need to separate one solvent composition from another.

The resin adsorbents useful in the process of the invention generally described above are macroreticular strong acid cation exchange resins having exchangeable cation substituents consisting essentially of from about 10% to about 90% heavy metal substituents and the remainder alkali metal and/or alkaline earth metal substituents.

The solvent and the percentage of heavy metal substituents in the resin adsorbent are selected to provide selectivity during adsorption and satisfactory desorption of adsorbed ester. Using a solvent of increased solubility parameter (especially increased polar and hydrogen bonding components) normally decreases adsorbing and increases desorbing. Increasing heavy metal percentage in the resin normally increases adsorbing and decreases desorbing. When a particular solvent has been selected, the percentage of heavy metal substituents is selected so as to be sufficiently high to provide desired selectivity during adsorption and sufficiently low to allow the solvent to cause desorption of adsorbed ester. When a particular resin and heavy metal substituent percentage has been selected, a solvent is selected having a solubility parameter and solubility parameter components sufficiently low to allow obtaining selectivity and sufficiently high so that desorption is obtained.

The selection of the combination of particular solvent and particular resin herein also allows obtaining desired selectivity and recovery of product while minimizing solvent recovery operations.

The process of this invention is preferably carried out continuously by a simulated moving bed unit operation.

The invention herein contemplates one stage processing as well as processing in a plurality of stages.

One stage processing is suitable for separating a mixture of two components or for separating a mixture of more than two components into two fractions.

Multistage processing is suitable for separating a mixture containing more than two components into more than two fractions.

An example of multistage processing is as follows: The feed to be separated is processed in a first stage with selected solvent and resin adsorbent to obtain first extract containing fraction enriched (compared to the feed) in ester of higher degree of unsaturation and first raffinate containing fraction enriched (compared to the feed) in ester of lesser degree of unsaturation and depleted (compared to the feed) in ester of higher degree of unsaturation. The first raffinate, preferably the ester fraction obtained by essentially completely removing solvent from first raffinate, is processed in a second stage with selected solvent and resin adsorbent to obtain second extract containing fraction enriched in ester of higher degree of unsaturation (compared to the ester fraction of the first raffinate) and second raffinate containing fraction enriched (compared to ester fraction of the first raffinate) in ester of lesser degree of unsaturation and depleted (compared to ester fraction of first raffinate) in ester of higher degree of unsaturation. To the extent succeeding stages are used, each succeeding stage has as its feed raffinate from the preceding stage, preferably ester fraction obtained by essentially completely removing solvent from such raffinate. If raffinate is stripped of solvent between stages so that the feed to a second or succeeding stage is ester fraction substantially free of solvent, then the solvent in one stage can be the same or different from the solvent in the other stage. The use of the same solvent in all stages has the advantage of minimizing the amount of stripping apparatus and storage capacity which is required.

In one important multistage process, two stages are used to provide three fractions, namely, a first fraction enriched in methyl ester of polyunsaturated fatty acid, a second fraction enriched in methyl ester of monounsaturated fatty acid and a third fraction enriched in methyl ester of saturated fatty acid (each fraction being compared to feed to the first stage). In this process, the feed into the first stage comprises methyl ester of saturated fatty acid (especially methyl stearate), methyl ester of monounsaturated fatty acid (especially methyl oleate), methyl ester of diunsaturated fatty acid (especially methyl linoleate) and methyl ester of triunsaturated fatty acid (especially methyl linolenate). In the first stage of this process, an extract is produced containing fraction enriched (compared to the feed into the first stage) in methyl ester of triunsaturated fatty (e.g. methyl linolenate) and in methyl ester of diunsaturated fatty acid (e.g. methyl linoleate), and a first raffinate is produced. In the second stage, ester fraction obtained on stripping solvent from first raffinate is the feed, and an extract is produced containing fraction enriched (compared to the feed into the first stage and compared to ester fraction of the first raffinate) in methyl ester of monounsaturated fatty acid (e.g. methyl oleate), and a second raffinate is produced containing fraction enriched (compared to the feed to the first stage and compared to ester fraction of the first raffinate) in methyl ester of saturated fatty acid (e.g. methyl stearate).

As used herein, the term "selectively" in the phrase "selectively adsorb" describes the ability of the adsorbent to preferentially adsorb a component or components. In practice, the component(s) which is (are) preferentially adsorbed, is (are) rarely ever the only component(s) adsorbed. For example, if the feed contains one part of a first component and one part of a second component, and 0.8 parts of the first component and 0.2 parts of the second component are adsorbed, the first component is selectively adsorbed. The degree of magnitude of selective adsorption is expressed herein in terms of relative selectivity, that is, the ratio of two components of the adsorbed phase (extract) divided by the ratio of the same two components in the unadsorbed phase (raffinate). In other words, relative selectivity as used herein is defined by the following equation:

$$\text{Selectivity} = \frac{[\text{Concentration } M/\text{Concentration } N]_A}{[\text{Concentration } M/\text{Concentration } N]_U}$$

where M and N are two components of the feed represented in volume or weight percent and the subscripts A and U represent the adsorbed and unadsorbed phases respectively. Such relative selectivity is readily obtained and calculated from pulse test data as described below. When the selectivity is 1.0, there is no preferential adsorption of one component over the other. A selectivity larger than 1.0 indicates preferential adsorption of component M; in other words, the extract phase is enriched in M and the raffinate phase is enriched in N. The farther removed the selectivity is from 1.0, the more complete the separation.

Separating "according to degree of unsaturation" is used herein to mean separating ester of higher degree of unsaturation from ester of lesser degree of unsaturation. The more double bonds in the carboxylic acid moiety, the higher is the degree of unsaturation. Thus, ester of triunsaturated (three double bonds in the carbon chain in the carboxylic acid moiety) fatty acid has a higher degree of unsaturation than ester of diunsaturated (two double bonds in the carbon chain in the carboxylic acid moiety) fatty acid which in turn has a higher degree of unsaturation than ester of monounsaturated (one double bond in the carbon chain in the carboxylic acid moiety) fatty acid which in turn has a higher degree of unsaturation than ester of saturated (no double bonds in the carbon chain in the carboxylic acid moiety) fatty acid.

The meaning of the terms "higher degree of unsaturation" and "lesser degree of unsaturation" as used herein depend on the context, that is the particular separation to which the invention is being applied. In a multistage process, the ester of higher degree of unsaturation in one stage may be different from the ester of higher degree of unsaturation in another stage. In the two stage process described above when the feed into the first stage comprises methyl linolenate, methyl linoleate, methyl oleate and methyl stearate, in the first stage the ester of higher degree of unsaturation is methyl linolenate and methyl linoleate and the ester of lesser degree of unsaturation is methyl oleate and methyl stearate, and in the second stage the ester of higher degree of unsaturation is methyl oleate and the ester of lesser degree of unsaturation is methyl stearate. The ester of higher degree of unsaturation has to include the ester of highest degree of unsaturation, and the ester of lesser degree of unsaturation has to include the ester of lowest degree of unsaturation. The ester of lesser degree of unsaturation includes ester of saturated fatty acid if such is present in the mixture being separated.

The terms "solubility parameter", "solubility parameter dispersion component", "solubility parameter polar component" and "solubility parameter hydrogen bonding component" as used herein are defined by equations 6-10 at page 891 of Kirk-Othmer, Encyclopedia of Chemical Technology, 2d edition, Supplement Volume published by Interscience Publishers (John Wiley & Sons), New York, 1971. Values herein for solubility parameter, solubility parameter dispersion component, solubility parameter polar component and solubility parameter hydrogen bonding component are for solvents at 25° C. (i.e., they are on a 25° C. basis). As at page 891, the symbols "$\delta$", "$\delta_D$", "$\delta_P$", and "$\delta_H$" are used herein to refer respectively to "solubility parameter", "solubility parameter dispersion component", "solubility parameter polar component", and "solubility parameter hydrogen bonding component". For many solvents the values for $\delta_D$, $\delta_P$ and $\delta_H$ are given in Table I which directly follows page 891 and the value for $\delta$ is calculated using equation (6) on page 891. For solvents consisting of a plurality of constituents, the values for "$\delta$", "$\delta_D$", "$\delta_P$" and "$\delta_H$" are calculated by summing the corresponding values for the constituents multiplied by their volume fractions.

The percentage of cationic substituents in a resin are percentages of total ion exchange capacity. Thus a resin having its exchangeable cation substituents consisting of 50% heavy metal substituents and 50% alkali metal substituents has 50% of its ion exchange capacity being taken up by heavy metal substituents and 50% of its ion exchange capacity being taken up by alkali metal substituents.

DETAILED DESCRIPTION

The fatty acid ester mixture which is to be separated according to the present process, that is the feed, contains esters having carbon chains in carboxylic acid moieties having different degrees of unsaturation. In other words, the feed is a mixture of ester of higher degree of unsaturation with ester of lesser degree of unsaturation.

The esters in the feed have the formula

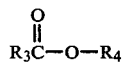

in which $R_3$ is an aliphatic chain which contains from 5 to 25 carbon atoms and is saturated (no double bonds in the aliphatic chain) or unsaturated (containing, for example, up to 5 double bonds in the aliphatic chain) and in which $R_4$ is an alkyl chain containing from 1 to 4 carbon atoms.

Esters in the feed herein can be, for example, methyl caproate, methyl caprylate, methyl caprate, methyl laurate, ethyl laurate, methyl myristate, methyl myristoleate, methyl palmitate, ethyl palmitate, methyl palmitoleate, methyl stearate, ethyl stearate, propyl stearate, isopropyl stearate, butyl stearate, methyl oleate, ethyl oleate, propyl oleate, isopropyl oleate, butyl oleate, methyl linoleate, ethyl linoleate, methyl linolenate, ethyl linolenate, methyl eleostearate, methyl arachidate, methyl gadoleate, methyl arachidonate, methyl behenate, methyl erucate, ethyl erucate, methyl clupanodonate, methyl lignocerate, methyl nisinate and methyl shibate.

The feed into a one stage process or into the first stage of a multistage process is readily obtained, for example, by alcoholysis of naturally occurring triglyceride (e.g. by reaction of naturally occurring fats and oils with excess methanol in the presence of sodium methoxide). Very important feeds are obtained by methanolysis of soybean oil, cottonseed oil, safflower oil and tallow. Feeds containing methyl esters are the most important commercially. One group of important feeds into the first stage of a multistage process comprises by weight (total fatty acid ester basis) from 0% to about 60% methyl linolenate, from about 2% to about 80% methyl linoleate, from about 5% to about 75% methyl oleate, and from about 1% to about 35% methyl stearate; such feeds often also comprise by weight (total fatty acid ester basis) from about 5% to about 30% methyl palmitate.

The feed into a one stage process or into any stage of a multistage process is preferably introduced into an adsorbing unit without solvent and is dissolved in solvent already in the unit, introduced for example, in a previous cycle to cause desorption. Introduction of feed without solvent is preferred because in most processes and especially in the continuous simulated moving bed process preferred herein, this has the advantage of increasing capacity and minimizing apparatus size. If desired, however, the feed can be dissolved in solvent prior to introduction into the adsorbing unit or the feed can be raffinate from a previous stage comprising ester mixture dissolved in solvent.

Turning now to the solvents useful herein, these are characterized by $\delta$ ranging from about 7.0 to about 10.5, $\delta_D$ ranging from about 7.0 to about 9.0, $\delta_P$ ranging from about 0.2 to about 5.1 and $\delta_H$ ranging from about 0.3 to about 7.4. Preferred solvents for use herein are characterized by $\delta$ ranging from about 7.5 to about 9.0, $\delta_D$ ranging from about 7.25 to about 8.0, $\delta_P$ ranging from about 1.0 to about 3.0, and $\delta_H$ ranging from about 1.0 to about 4.0.

One important group of solvents are those consisting essentially by volume of from 0% to about 90% $C_5$-$C_{10}$ hydrocarbon (that is, hydrocarbon with from 5 to 10 carbon atoms) and from 100% to about 10% carbonyl group containing compound selected from the group consisting of (a) ester having the formula

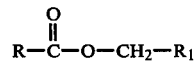

wherein R is hydrogen or alkyl chain containing one or two carbon atoms and $R_1$ is hydrogen or alkyl chain containing one to three carbon atoms and (b) ketone having the formula

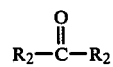

wherein each $R_2$ is the same or different and is alkyl chain containing 1 to 5 carbon atoms. Examples of suitable hydrocarbons are pentane, hexane, heptane, octane, nonane, decane, 1-hexene, 1-heptene, benzene and toluene. Examples of esters suitable for use in or as the solvent are methyl formate, methyl acetate, ethyl acetate, methyl propionate, propyl formate and butyl formate. Examples of ketones suitable for use in or as the solvent are acetone, methyl ethyl ketone, methyl isobutyl ketone and diethyl ketone. Preferred is a solvent consisting essentially by volume of from 0% to about 60% hydrocarbon and from about 100% to about 40% ester. A very preferred solvent is 100% ethyl acetate.

Another very preferred solvent consists essentially by volume of from about 15% to about 60% hexane with the remainder being ethyl acetate.

Another important group of solvents are chlorinated hydrocarbons containing 1 or 2 carbon atoms and 2 or 3 chlorine substituents and blends of these chlorinated hydrocarbons with up to about 90% by volume $C_5$–$C_{10}$ hydrocarbons. Specific examples of solvents within this group are methylene dichloride, trichloroethylene, 1,1-dichloroethane and 1,1,1-trichloroethane and blends of methylene dichloride and hexane.

Still another important group of solvents are dialkyl ethers containing 1 to 3 carbon atoms in each alkyl group. Specific examples of solvents within this group are diethyl ether and diisopropyl ether.

Yet another important group of solvents are blends of $C_{1-3}$ alcohols (e.g. from about 5% to about 35% by volume alcohol) and esters having the formula

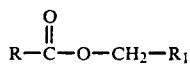

where R and $R_1$ are as defined above. Specific examples of solvents within this group are blends of methanol or ethanol with ethyl acetate.

As previously indicated, the solvent performs a dual role. Firstly, it is the dissolving phase during adsorption. Secondly, it is the vehicle for desorption (the desorbent).

In most continuous processes envisioned within the scope of the invention, the solvent is introduced into the process in a desorbing zone and sufficient solvent remains in the process to perform at a downstream location the dissolving function for adsorption.

The solvent to feed ratio generally ranges on a volume basis from about 4:1 to about 20:1 and preferably ranges from about 8:1 to about 15:1.

The term "solvent" as used herein refers both to solvent blends (i.e., solvents consisting of a plurality of constituents) and the pure compounds (i.e., solvents consisting of a single constituent) unless the context indicates otherwise.

Turning now to the adsorbent, resin used as adsorbent herein has a matrix obtained by polymerizing styrene and divinyl benzene monomers and then sulfonating. The resin is highly cross-linked. It is macroporous and has a high surface area (surface areas are greater than 20 $m^2$/gm and usually are in the range of 250–1000 $m^2$/gm). Typical resins which can be obtained commercially for conversion into the adsorbents useful herein have ion exchange capacities ranging from about 3 to about 6 milliequivalents per gram (dry basis) and are sold under tradenames such as Amberlyst 15, Amberlyst XN1005 and Amberlyst XN1010 (all available from Rohm & Haas) and MSC-1 (available from Dow Chemical).

As indicated hereinbefore, resin useful herein as adsorbent has its exchangeable cation substituents consisting essentially of (a) heavy metal substituents and (b) alkali metal and/or alkaline earth metal substituents. The heavy metal substituents can be referred to as active substituents since they provide a charge which participates in causing adsorption. The alkali metal and alkaline earth metal substituents can be referred to as spacing substituents since they regulate the amount of adsorbing power thereby regulating selectivity during adsorption and ability to desorb. The alkali metal and alkaline earth metal substituents also stabilize the resin by being present instead of hydrogen; it is important that the adsorbent contain no resin even partly in the hydrogen form since hydrogen form resin is a very strong catalyst and promotes side reactions. Preferred heavy metal substituents are copper, gold and silver in a valence state of one; silver is most preferred. Preferred alkali metal and alkaline earth metal substituents are sodium and potassium in a valence state of one and calcium, barium and magnesium in a valence state of two; sodium is most preferred. The most preferred resin has silver as its heavy metal substituent and sodium as the remaining cationic substituent.

As previously indicated, the resin adsorbent has its exchangeable cation substituents consisting essentially of from about 10% to about 90% heavy metal substituents and the remainder alkali metal and/or alkaline earth metal substituents with the percentages being percentages of ion exchange capacity. Preferably, the resin adsorbent has its exchangeable cation substituents consisting essentially of from about 20% to about 85% heavy metal substituents and the remainder alkali metal and/or alkaline earth metal substituents. Sufficient heavy metal substituents should be present to cause selective adsorption of the component(s) desired to be adsorbed but not so much that a major proportion of other component(s) will be adsorbed concurrently and not so much that adsorbed component(s) cannot be desorbed. The particular allocation between heavy metal cation substituents and spacing cation substituents (alkali metal and/or alkaline earth metal cation substituents) to be selected depends on the mixture being separated. Such allocation also depends on the solvent being utilized. The selected allocation can vary between types and batches of commercially obtained resin used to prepare adsorbent. The general lower limit of about 10% is selected herein because no separation is envisioned where percentages of heavy metal substituents lower than this would be sufficient to cause adsorption of component desired to be adsorbed. The general upper limit of about 90% is selected herein because no separation is envisioned where a percentage of heavy metal substituents higher than this would provide superior selectivity and at the same time would allow satisfactory desorption.

Examples of specific resins useful herein as adsorbents are Amberlyst XN1010 with 30% silver substitution and 70% sodium substitution, Amberlyst XN1010 with 50% silver substitution and 50% sodium substitution, Amberlyst XN1010 with 70% silver substitution and 30% sodium substitution, Amberlyst XN1005 with 50% silver substitution and 50% sodium substitution, Amberlyst 15 with 50% silver substitution and 50% sodium substitution, Amberlyst XN1010 with 50% silver substitution and 50% potassium substitution, Amberlyst XN1005 with 50% copper substitution and 50% sodium substitution, Amberlyst 15 with 30% gold substitution and 70% sodium substitution, Amberlyst XN1010 with 50% silver substitution and 50% barium substitution, Amberlyst XN1010 with 40% silver substitution and 60% calcium substitution and Amberlyst XN1010 with 60% silver substitution and 40% magnesium substitution.

The resins useful as adsorbents herein are readily prepared, for example, from commercially available macroreticular cation exchange resins (some of which are listed above). Such preparation simply involves exchange to supply the proper cation substituents. If the commercially obtained resin is in the hydrogen form, it is first converted to the form of the cation substituent which is displaceable by the second cation which is to be introduced as a substituent, then such second cation is introduced to the degree desired. For example, if a 50% silver substituted, 50% sodium substituted resin (percentages are percentages of total ion exchange capacity) is desired, it can be made as follows: hydrogen form resin is first converted to sodium form, for example, by flushing with 10% sodium hydroxide solution and washing, then the sodium form resin is treated with a predetermined amount of silver nitrate in a batch equilibrium soak to introduce the desired percentage of silver; if sodium form resin is commercially obtained, such resin is simply treated with silver nitrate as above to obtain the desired degree of silver substitution.

The resins useful as adsorbents herein generally have particle sizes ranging from 20 mesh to 200 mesh (U.S. Sieve Series). For a continuous process, particle sizes of about 30 mesh to about 80 mesh (U.S. Sieve Series) are preferred; using particle sizes larger than about 30 mesh causes process velocity limitations and using particle sizes less than about 80 mesh results in high pressure drops. Usually the particle size used is about the same as that of a commercially obtained resin treated to introduce the selected cation substituents; in other words, introduction of cation substituents does not change particle size to any significant extent.

The particular resin adsorbent selected herein and particular solvent selected herein interact and cooperate to provide an operative process with a number of advantages. The resin only being partially substituted with heavy metal allows selectivity to be obtained and allows desorption to be obtained with the selected solvent and allows a savings on the amount of heavy metal utilized. The particular selected solvent allows selectivity to be obtained at the partial level of heavy metal substitution, allows desorption to be obtained at such partial level of heavy metal substitution and does not have a deleterious effect on the resin (does not attack it). The combination allows the same solvent to be used during adsorption and desorption so that a commercial process can be carried out without the need to separate one solvent from another.

We turn now to the processing conditions of temperature and pressure. The temperatures utilized during adsorbing and during desorbing can be the same and generally range from about 20° to about 150° C. A preferred temperature range to be used when the feed is a mixture of methyl esters having fatty acid moieties with aliphatic chains having from 12 to 20 carbon atoms, is about 50° to about 80° C. Lower temperatures within the above-described broad range are preferably utilized when the solvent comprises ketone. The pressures utilized during adsorbing and desorbing can be the same and generally range from atmospheric (14.7 psia) to about 500 psia. For a simulated moving bed process as described hereafter, the pressures utilized preferably range from about 30 psia to about 120 psia.

For a batch process, sufficient residence times should be provided to get high yields and purities. The rates for continuous processing are a function of the size of the equipment and the liquid flow rates.

As previously indicated, processing herein gives a raffinate and an extract. The raffinate contains fraction which is enriched in content of ester of lesser degree of unsaturation. It comprises esters which were weakly attracted by the adsorbent, dissolved in solvent. The extract contains fraction enriched in content of ester of higher degree of unsaturation. It comprises esters which were more strongly attracted by the adsorbent, dissolved in solvent. The fractions of ester can be recovered from the raffinate and from the extract by conventional separation processes such as by stripping solvent with heat and vacuum and then distilling.

Turning now to batch processing, this is readily carried out in equipment conventionally used for adsorptions carried out batchwise. For example, such processing can be carried out utilizing a column containing resin adsorbent with intermittent flow of feed and solvent therethrough.

Continuous processing can be carried out in conventional continuous adsorbing apparatus. One type of continuous processing is the simulated moving bed process referred to earlier as the preferred process for carrying out the present invention. A simulated moving bed unit operation and apparatus for such useful herein is described in Broughton et al U.S. Pat. No. 2,985,589.

For a simulated moving bed embodiment of this invention, preferred apparatus includes (a) at least four columns connected in series, each containing a bed of resin; (b) liquid access lines communicating with an inlet line to the first column, with an outlet line from the last column and with the connecting lines between successive columns; (c) a recirculation loop including a variable speed pump, providing communication between the outlet line from the last column and the inlet line to the first column; and (d) means to regulate what flows in or out of each liquid access line.

Such preferred simulated moving bed apparatus is operated so that liquid flow is in one direction and so that countercurrent flow of resin is simulated by manipulation of what goes into and out of the liquid access lines. More particularly, the apparatus is operated so that four functional zones are in operation. The first of the functional zones is usually referred to as the adsorption zone. This zone is downstream of a feed inflow and upstream of a raffinate outflow. In the adsorption zone, ther is a net and selective adsorption of ester of higher degree of unsaturation and a net desorption of solvent and of ester of lesser degree of unsaturation. The second of the functional zones is usually referred to as the purification zone. It is downstream of an extract outflow and upstream of the feed inflow and just upstream of the adsorption zone. In the purification zone, ester of higher degree of unsaturation which has previously been desorbed is preferentially adsorbed and there is a net desorption of solvent and of ester of lesser degree of unsaturation. The third of the functional zones is referred to as the desorption zone. It is downstream of a solvent inflow and upstream of the extract outflow and just upstream of the purification zone. In the desorption zone, there is a net desorption of ester of higher degree of unsaturation and a net adsorption of solvent. The fourth functional zone is usually referred to as the buffer zone. It is downstream of the raffinate outflow and upstream of the solvent inflow and just upstream of the desorption zone. In the buffer zone, ester of lesser degree of unsaturation is adsorbed and solvent is desorbed. The various liquid access lines are utilized to provide the feed inflow between the purification and adsorption zones, the raffinate outflow between the adsorption and buffer zones, the solvent inflow between the buffer and desorption zones and the extract outflow between the desorption and purification zones. The liquid flow is manipulated at predetermined time periods and the speed of the pump in the recirculation loop is varied concurrent with such manipulation so that the inlet points (for feed and solvent) and the outlet points (for raffinate and extract) are moved one position in the direction of liquid flow (in a downstream direction) thereby moving the aforedescribed zones in the direction of liquid flow and simulating countercurrent flow of resin adsorbent.

Less preferred continuous simulated moving bed apparatus than described above is the same as the apparatus described above except that only sufficient columns are provided to accommodate adsorption, purification and desorption zones and recirculation means is omitted. Such apparatus is operated with adsorption, purification and desorption zones; the buffer zone is omitted.

In the operation of the above described simulated moving bed processes, the relative number of columns in each zone to optimize a process is ordinarily selected by trial and error. One factor in selecting the number of columns in the adsorption zone is the percentage of the feed to be adsorbed. The purity of the extract and raffinate streams is a function of the number of columns in the adsorption zone. The longer the adsorption zone (the more columns in it), that is, the further removed the feed inlet is from the raffinate outlet, the purer the raffinate is.

In the operation of the above described simulated moving bed processes, the time interval between manipulations of liquid flow should be sufficient to allow a substantial proportion of ester of higher degree of unsaturation to stay in the adsorption zone and a substantial proportion of ester of lesser degree of unsaturation to leave. Such time interval can be calculated using pulse test (described later) data.

We turn now in more detail to the two stage process referred to generally above.

As previously indicated, in such two stage process the feed into the first stage is a mixture comprising methyl ester of saturated fatty acid, methyl ester of monounsaturated fatty acid, methyl ester of diunsaturated fatty acid and methyl ester of triunsaturated fatty acid. This process preferably comprises (a) in a first stage:
(i) contacting a solution of said mixture in solvent with macroreticular strong acid cation exchange resin to selectively adsorb methyl ester of triunsaturated fatty acid and methyl ester of diunsaturated fatty acid and to leave in solution in solvent a fraction of said mixture enriched in content of methyl ester of monounsaturated fatty acid and methyl ester of saturated fatty acid and depleted in content of methyl ester of triunsaturated fatty acid and methyl ester of diunsaturated fatty acid,
(ii) removing from contact with the resin a solution in solvent of fraction enriched in content of methyl ester of monounsaturated fatty acid and methyl ester of saturated fatty acid and depleted in content of methyl ester of triunsaturated fatty acid and methyl ester of diunsaturated fatty acid and withdrawing such solution as a first raffinate,
(iii) contacting resin which has selectively adsorbed methyl ester of triunsaturated fatty acid and methyl ester of diunsaturated fatty acid with solvent to cause desorption of methyl ester of triunsaturated fatty acid and methyl ester of diunsaturated fatty acid and provide a solution in the solvent of fraction enriched in content of methyl ester of triunsaturated fatty acid and methyl ester of diunsaturated fatty acid,
(iv) removing solution in solvent of fraction enriched in content of methyl ester of triunsaturated fatty acid and methyl ester of diunsaturated fatty acid from contact with resin;

the solvent in each step of the first stage having the same composition; the resin in the first stage having its exchangeable cation substituents consisting essentially of from about 10% to about 60% silver substituents and the remainder sodium substituents;

(b) essentially completely removing solvent from first raffinate leaving fatty acid ester mixture enriched in content of methyl ester of monounsaturated fatty acid and methyl ester of saturated fatty acid and depleted in content of methyl ester of triunsaturated fatty acid and methyl ester of diunsaturated fatty acid;

(c) in a second stage:
(i) contacting a solution of fatty acid ester mixture from step (b) in solvent with macroreticular strong acid cation exchange resin to selectively adsorb methyl ester of monounsaturated fatty acid and leave in solution a fraction enriched in content of methyl ester of saturated fatty acid and depleted in content of methyl ester of monounsaturated fatty acid,
(ii) removing from contact with the resin a solution in solvent of fraction which is enriched in content of methyl ester of saturated fatty acid and depleted in content of methyl ester of monounsaturated fatty acid,
(iii) contacting resin which has selectively adsorbed methyl ester of monounsaturated fatty acid with solvent to cause desorption of methyl ester of monounsaturated fatty acid and provide a solution in the solvent of fraction enriched in content of methyl ester of monounsaturated fatty acid,
(iv) removing solution of fraction enriched in content of methyl ester of monounsaturated fatty acid from contact with resin;

the solvent in each step of the second stage having the same composition; the resin in the second stage having its exchangeable cation substituents consisting essentially of about 40% to about 85% silver substituents and the remainder sodium substituents; the solvent in one stage being the same or different from the solvent in the other stage; the solvent in each stage consisting essentially by volume of from 0% to about 90% $C_5$-$C_{10}$ hydrocarbon and from 100% to about 10% carbonyl group containing compound selected from the group consisting of (a) ester having the formula

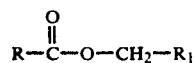

wherein R is hydrogen or alkyl chain containing one or two carbon atoms and $R_1$ is hydrogen or alkyl chain containing from one to three carbon atoms and (b) ketone having the formula

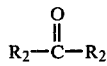

wherein each $R_2$ is the same or different and is alkyl chain containing from 1 to 5 carbon atoms; the solvent and percentage of silver substituents for each stage being selected to provide selectivity in step (i) and desorption in step (iii). The broad range of silver substituents specified for each stage accommodates for the difference in ion exchange capacities of the resins which may be used to provide the matrix for the adsorbent resins.

The process described in the above paragraph is preferably carried out with each stage constituting a continuous simulated moving bed unit operation as described above. One group of important feeds for this process is the group of feeds comprising methyl linolenate, methyl linoleate, methyl oleate and methyl stearate. A very important species of this group of feeds is derived from soybean oil and blends of soybean oil with other fats and/or oils and comprises by weight (total fatty acid ester basis) from about 4% to about 15% methyl linolenate, from about 40% to about 65% methyl linoleate, from about 12% to about 35% methyl oleate, from about 2% to about 10% methyl stearate and from about 10% to about 25% methyl palmitate; in such case, the first raffinate comprises by weight (total fatty acid ester basis) from 0% to about 4% methyl linolenate, from 0% to about 5% methyl linoleate, from about 20% to about 70% methyl oleate, from about 4% to about 20% methyl stearate, and from about 40% to about 70% methyl palmitate. In a very preferred embodiment, the solvent in each stage is ethyl acetate, the resin in the first stage has its exchangeable cation substituents consisting essentially of from about 40% to about 60% silver substituents and the remainder sodium substituents, and the resin in the second stage has its exchangeable cation substituents consisting essentially of from about 65% to about 85% silver substituents and the remainder sodium substituents. In another embodiment, the solvent in each stage is the same and consists essentially by volume of from about 15% to about 60% hexane with the remainder being ethyl acetate.

The term "pulse test" is used above and in Examples I, II and III below. This is a test used to determine the quality of separation that can be obtained for a particular feed with a selected adsorbent and solvent. In this test the apparatus utilized comprises a column which is packed with adsorbent and which has inlet and outlet ports at its opposite ends. The column is in a temperature controlled environment. A constant flow pump is used to pump liquid through the column at a predetermined flow rate. In the conducting of a pulse test the adsorbent is allowed to come to equilibrium with a particular solvent by passing the solvent through a column for a predetermined period of time. At a convenient time after such equilibrium is obtained, a pulse of feed containing a known amount of tracer is injected, via a sample coil, into the solvent inflow (without stopping the solvent flow). The pulse of feed plus tracer is thereby caused to flow through the column with components being first adsorbed by the adsorbent and then caused to be desorbed by the solvent. Equal volume effluent samples are collected and analyzed by gas chromatography. From these analyses, elution concentration curves for ester components and tracer are obtained (concentration in milligrams per milliliter is plotted on the y axis and elution volume in milliliters is plotted on the x axis). The distance from time zero (the time when the pulse of feed plus tracer is introduced) to the peak of the curve for a component is the elution volume for that component. The difference between the elution volume for an ester component and the elution volume for the tracer is the retention volume of that ester component. The relative selectivity of one ester component over another (when the selected adsorbent and solvent are utilized) is the ratio of their respective retention volumes.

The invention is illustrated by the following specific examples,

In Examples I, II and III, plulse tests are run. The column for the pulse tests has a length of 120 cm. and an inside diameter of 1 cm. It is packed with about 60 grams of resin adsorbent (dry basis).

In Example IV, a pilot plant test apparatus or demonstration unit is mentioned. This is apparatus operated according to the continuous simulated moving bed unit operation mentioned above. The apparatus comprises 24 columns which are connected in series in a loop to permit the process liquid to flow in one direction. Each column has a length of 12 inches and an inside diameter of 9/10 of an inch and is loaded with about 70 grams of resin adsorbent (dry basis). Each column is equipped with a four-position valve connected to two inlet and two outlet conduits. When such valve is closed, liquid flows only toward the next succeeding column. By selecting between the four open positions, feed can be caused to be introduced to the system (e.g. position 1), solvent can be caused to be introduced to the system (e.g. position 2), a raffinate stream can be removed from the system (e.g. position 3) or an extract stream can be removed from the system (e.g. position 4). Backflow control valves are located in the inter-column connectors. These are used to close off columns from process liquid flow to isolate the high pressure inlet (solvent) from the low pressure outlet to accommodate for no buffer zone being used. The unit is operated in Example IV as follows: At any time it constitutes a single stage. It is operated only with the three required working zones (adsorption, purification and desorption). In other words, no buffer zone is used and one backflow control valve is always in closed position to close off two columns from the process flow to accommodate for this. No recirculation is used. The 22 columns that are on stream are apportioned between the adsorption, purification and desorption zones as described above with a selected number of columns in series comprising each zone. Feed is introduced into the first column of the adsorption zone and is dissolved in solvent and is contacted with resin adsorbent. As liquid flows downstream through the adsorption zone, component(s) of higher degree of unsaturation is (are) selectively adsorbed leaving raffinate enriched in ester of lesser degree of unsaturation. In the purification zone, nonadsorbed components are forced from the adsorbent and are thus forced downstream toward the feet point. The extract is removed at the inlet to the purification zone and is enriched in adsorbed components. The solvent is added at the inlet to the desorption zone and causes desorption of adsorbed component(s) from the adsorbent for removal downstream at the extract point. At selected intervals a controller advances the flow pattern (into and out of columns) one column (in other words, the controller manipulates valves so that raffinate outflow, feed inflow, extract outflow and solvent inflow points each advance one step, that is, to the next liquid access point in the direction of liquid flow) to "step forward" to keep pace with the liquid flow. Twenty-four "steps" constitute a cycle. The "step time" is chosen from pulse test data such as to allow the non-adsorbed components to advance faster than the feed point and reach the raffinate point. The adsorbed ester moves slower than the feed point and falls behind the extract point.

EXAMPLE I

Pulse tests were run with ethyl acetate ($\delta=8.85$; $\delta_D=7.70$; $\delta_P=2.60$; $\delta_H=3.50$) as the solvent and Amberlyst XN1010 resin (from a first batch) having various levels of silver and sodium substitution as adsorbents.

In each test, the feed was derived from soybean oil and consisted by weight (total fatty acid ester basis) of 1% methyl ester of saturated $C_{14}$ and lower fatty acid, 12% methyl palmitate, 4% methyl stearate, 25% methyl oleate, 52% linoleate and 6% methyl linolenate.

Tests were run on three different resin adsorbents: the Amberlyst XN1010 (a macroporous, styrene-divinyl benzene sulfonic acid cation exchange resin manufactured by Rohm & Haas), screened to through 20 and on 40 mesh (U.S. Sieve Series), having its exchangeable cation substituents consisting of 15% silver substituents (valence state of one) and 85% sodium substituents (Test 1); the Amberlyst XN1010, screened to through 20 and on 40 mesh (U.S. Sieve Series) having its exchangeable cation substituents consisting of 30% silver substituents (valence state of one) and 70% sodium substituents (Test 2); and the Amberlyst XN1010, screened to through 20 and on 40 mesh (U.S. Sieve Series), having its exchangeable cation substituents consisting of 50% silver substituents (valence state of one) and 50% sodium substituents (Test 3). In each case the resin adsorbent was prepared by screening resin beads to isolate a through 20 and on 40 mesh fraction, converting such fraction to the sodium form by exchange with an excess of sodium hydroxide, then introducing the desired level of silver by equilibrium contact with silver nitrate solution, then drying in a 105° C. air oven for 12–16 hours.

In each test, the resin adsorbent was dispersed in ethyl acetate solvent, allowed to swell and introduced as a dispersion in swelled form into the column.

Each test was run at 75° C.

In each test, solvent was pumped continuously through the column at a rate of 2 ml. per minute. At time zero, a sample pulse of 1 ml. containing approximately 0.025 grams docosane (a linear hydrocarbon tracer) and 0.250 grams methyl ester feed mixture dissolved in ethyl acetate was added by means of the sample coil into the solvent flow. The equal volume samples that were collected and analyzed were each 5 ml.

In Test 1, retention volumes were obtained as follows: for methyl palmitate, 7.5 ml.; for methyl stearate, 7.5 ml.; for methyl oleate, 7.5 m.; for methyl linoleate, 7.5 ml.; and for methyl linolenate, 7.5 ml.

In Test 1, relative selectivities were obtained as follows: for methyl oleate/methyl palmitate, 1.0; for methyl linoleate/methyl palmitate, 1.0; for methyl linolenate/methyl palmitate, 1.0; for methyl linoleate/methyl oleate, 1.0; for methyl linolenate/methyl linoleate, 1.0.

In Test 2, retention volumes were obtained as follows: for methyl palmitate, 5.0 ml.; for methyl stearate, 5.0 ml.; for methyl oleate, 7.5 ml.; for methyl linoleate, 10.0 ml.; and for methyl linolenate, 27.5 ml.

In Test 2, relative selectivities were obtained as follows: for methyl oleate/methyl palmitate, 1.5; for methyl linoleate/methyl palmitate, 2.0; for methyl linolenate/methyl palmitate, 5.5; for methyl linoleate/methyl oleate, 1.3; for methyl linolenate/methyl linoleate, 2.8.

In Test 3, retention volumes were obtained as follows: for methyl palmitate, 2.5 ml.; for methyl stearate 2.5 ml.; for methyl oleate, 10.0 ml.; for methyl linoleate 35.0 ml. Methyl linolenate did not elute in measurable peak.

In Test 3, relative selectivities were obtained as follows: for methyl oleate/methyl palmitate, 4.0; for methyl linoleate/methyl palmitate 14.0; for methyl linoleate/methyl oleate, 3.5.

The above retention volumes and selectivities indicate that good separation of methyl linolenate from methyl linoleate, methyl oleate, methyl stearate and methyl palmitate is obtained using ethyl acetate and Amberlyst XN1010 resin (first batch) with 30% silver substitution and 70% sodium substitution and that good separation of methyl linoleate from methyl oleate, methyl stearate and methyl palmitate is obtained using ethyl acetate and Amberlyst XN1010 resin (first batch) with 50% silver substitution and 50% sodium substitution. By plotting retention volume differences vs. percentage silver substitution and extrapolating, it is indicated that good separation of methyl oleate from methyl stearate and methyl palmitate is obtained using ethyl acetate and Amberlyst XN1010 resin (first batch) with 80% silver substitution and 20% sodium substitution.

When in the tests of the above example, an equivalent amount of copper or gold is substituted for the silver as the heavy metal substituent of the resin adsorbent, results are obtained indicating good separation in each of the instances indicated above.

When in the tests of the above example, an equivalent amount of potassium, barium, calcium or magnesium is substituted for the sodium substituent of the resin adsorbent, results are obtained indicating good separation in each of the instances indicated above.

When in the tests of the above example, the solvent consists by volume of 50% ethyl acetate and 50% hexane, (for this solvent blend: $\delta=7.81$; $\delta_D=7.50$; $\delta_P=1.30$ and $\delta_H=1.75$), good separation of methyl linolenate from the less unsaturated esters is demonstrated to be obtained with resin having its exchangeable cation substituents consisting of 20% silver (valence state of one) substituents and 80% sodium substituents, good separation of methyl linoleate from the less unsaturated esters is demonstrated to be obtained with resin having its exchangeable cation substituents consisting of 40% silver (valence state of one) substituents and 60% sodium substituents, and good separation of methyl oleate from the less unsaturated esters is demonstrated to be obtained with resin having its exchangeable cation substituents consisting of 70% silver (valence state of one) substituents and 30% sodium substituents.

EXAMPLE II

Pulse tests were run with ethyl acetate as the solvent and Amberlyst XN1010 resin (from a second batch) having various levels of silver and sodium substitution as adsorbent.

In each test, the feed was derived from safflower oil and consisted by weight (total fatty acid ester basis) of 7% methyl palmitate, 2.5% methyl stearate, 12.5% methyl oleate and 78.0% methyl linoleate.

Tests were run on three different resin adsorbents: the Amberlyst XN1010 (a macroporous, styrene-divinyl benzene sulfonic acid cation exchange resin manufactured by Rohm & Haas), screened to through 20 and on 40 mesh (U.S. Sieve Series), having its exchangeable cation substituents consisting of 25% silver substituents (valence state of one) and 75% sodium substituents (Test 1); the Amberlyst XN1010, screened to through 20 and on 40 mesh (U.S. Sieve Series), having its exchangeable cation substituents consisting of 50% silver substituents (valence state of one) and 50% sodium substituents (Test 2); and the Amberlyst XN1010, screened to through 20 and on 40 mesh (U.S. Sieve Series), having its exchangeable cation substituents consisting of 75% silver substituents (valence state of one) and 25% sodium substituents (Test 3). In each case the resin adsorbent was prepared by screening resin beads to isolate a through 20 and on 40 mesh fraction, converting such fraction to the sodium form by exchange with an excess of sodium hydroxide, then introducing the desired level of silver by equilibrium contact with silver nitrate solution, then drying in a 105° C. air oven for 12-16 hours.

In each test, the resin adsorbent was dispersed in ethyl acetate solvent, allowed to swell and introduced as a dispersion in swelled form into the column.

Each test was run at 75° C.

In each test, solvent was pumped continuously through the column at a rate of 2 ml. per minute. At time zero, a sample pulse of 1 ml. containing approximately 0.08 grams docosane (a linear hydrocarbon tracer) and 0.80 grams methyl ester feed mixture was added by means of the sample coil into the solvent flow. The equal volume samples that were collected and analyzed were each 5 ml.

In Test 1, retention volumes were obtained as follows: methyl palmitate, 2.0 ml.; methyl stearate, 2.0 ml.; methyl oleate, 2.5 ml.; methyl linoleate, 3.0 ml.

In Test 1, relative selectivities were obtained as follows: methyl oleate/methyl palmitate, 1.3; methyl linoleate/methyl palmitate, 1.5; methyl linoleate/methyl oleate, 1.2.

In Test 2, retention volumes were obtained as follows: methyl palmitate, 6.0; methyl stearate, 6.0; methyl oleate, 8.5; methyl linoleate, 18.5.

In Test 2, relative selectivities were obtained as follows: methyl oleate/methyl palmitate, 1.4; methyl linoleate/methyl palmitate, 3.1; methyl linoleate/methyl oleate, 2.2.

In Test 3, retention volumes were obtained as follows: methyl palmitate, 3.5; methyl stearate, 3.5; methyl oleate, 18.5, and methyl linoleate, 81.0 (approximately elution volume for a very broad curve).

In Test 3, relative selectivities were obtained as follows: methyl oleate/methyl palmitate, 5.3; methyl linoleate/methyl palmitate, 23.1; methyl linoleate/methyl oleate, 4.4.

The above retention volumes and selectivities indicate that good separation of methyl linoleate from methyl oleate occurs using ethyl acetate as solvent with Amberlyst XN1010 (second batch) having its exchangeable cation substituents within the range of from 50% to 65% silver substituents and the remainder sodium substituents and that good separation of methyl oleate from methyl palmitate (and stearate) occurs using ethyl acetate as solvent with Amberlyst XN1010 (second batch) having its exchangeable cation substituents consisting of 70 to 80% silver substituents and the remainder sodium substituents.

EXAMPLE III

Pulse tests were run with solvent consisting by volume of 50% ethyl acetate and 50% hexane and with Amberlyst XN1010 resin (from a second batch) having various levels of silver and sodium substitution as absorbent.

In each test, the feed was derived from safflower oil and consisted by weight (total fatty acid ester basis) of 7% methyl palmitate, 2.5% methyl stearate, 12.5% methyl oleate and 78.0% methyl linoleate.

Tests were run on three different resin absorbents: the Amberlyst XN1010 (a macroporous, styrene-divinyl benzene sulfonic acid cation exchange resin manufactured by Rohm & Haas), screened to through 20 and on 40 mesh (U.S. Sieve Series), having its exchangeable cation substituents consisting of 25% silver substituents (valence state of one) and 75% sodium substituents (Test 1); the Amberlyst XN1010, screened to through 20 and on 40 mesh (U.S. Sieve Series), having its exchangeable cation substituents consisting of 50% silver substituents (valence state of one) and 50% sodium substituents (Test 2); and the Amberlyst XN1010, screened to through 20 and on 40 mesh (U.S. Sieve Series), having its exchangeable cation substituents consisting of 75% silver substituents (valence state of one) and 25% sodium substituents (Test 3). In each case the resin adsorbent was prepared by screening resin beads to isolate a through 20 and on 40 mesh fraction, converting such fraction to the sodium form by exchange with an excess of sodium hydroxide, then introducing the desired level of silver by equilibrium contact with silver nitrate solution, then drying in a 105° C. air oven for 12-16 hours.

In each test, the resin adsorbent was dispersed in ethyl acetate hexane solvent mixture, allowed to swell and introduced as a dispersion in swelled form into the column.

Each test was run at 75° C.

In each test, solvent was pumped continuously through the column at a rate of 2 ml. per minute. At time zero, a sample pulse of 1 ml. containing approximately 0.08 grams docosane (a linear hydrocarbon tracer) and 0.80 grams methyl ester feed mixture was added by means of the sample coil into the solvent flow. The equal volume samples that were collected and analyzed were each 5 ml.

In Test 1, retention volumes were obtained as follows: methyl palmitate, 2.5 ml.; methyl stearate, 2.5 ml.; methyl oleate, 2.5 ml.; and methyl linoleate, 5.0 ml.

In Test 1, relative selectivities were obtained as follows: methyl oleate/methyl palmitate, 1.0; methyl linoleate/methyl palmitate, 2.0; methyl linoleate/methyl oleate, 2.0.

In Test 2, retention volumes were obtained as follows: methyl palmitate, 3.5 ml.; methyl stearate, 3.5 ml.; methyl oleate, 6.0 ml.; methyl linoleate, 18.0 ml.

In Test 2, relative selectivities were obtained as follows: methyl oleate/methyl palmitate, 1.7; methyl linoleate/methyl palmitate, 5.1; methyl linoleate/methyl oleate, 3.0.

In Test 3, retention volumes were obtained as follows: methyl palmitate, 5.0 ml.; methyl stearate, 2.5 ml.; methyl oleate, 14.5 ml.; and methyl linoleate, 60.0 ml.

In Test 3, relative selectivities were obtained as follows: methyl oleate/methyl palmitate, 2.9; methyl linoleate/methyl palmitate, 12.0; methyl linoleate/methyl oleate, 4.1.

The above retention volumes and selectivities indicate that good separation of methyl linoleate from methyl oleate is obtained with 50% hexane-50% ethyl acetate solvent and Amberlyst XN1010 (second batch) with 50% silver and 50% sodium substitution.

EXAMPLE IV

This example illustrates the two stage process described in detail above. It involves the two-stage separation of a mixture comprising methyl linolenate, methyl linoleate, methyl oleate, and methyl stearate into three product fractions, namely, the polyunsaturates, the monounsaturates, and the saturates.

The demonstration unit described above is utilized for each stage and in each stage its operation is as generally described above.

In the first stage: The feed composition is derived from soybean oil and consists by weight of 17.0% methyl palmitate, 3.3% methyl stearate, 13.7% methyl oleate, 60.4% methyl linoleate, 5.5% methyl linolenate and 0.1% other. The solvent is ethyl acetate. The resin adsorbent is Amberlyst XN1010 (first batch) exchanged to 50% silver (valence state of 1) and 50% sodium; it has a particle size of through 20 and on 40 mesh (U.S. Sieve Series). The controller and valves of the demonstration unit are set so that the desorption zone includes four columns, the purification zone includes six columns and the adsorption zone includes 12 columns. The step time (the interval at which the flow pattern is advanced one column) is 5 minutes and 45 seconds. The feed rate is 1.5 ml. per minute. The solvent introduction rate is 25.3 ml. per minute. The solvent to feed ratio is 16.9 to 1. The extract flow is 13.6 ml./minute. The raffinate flow is 13.2 ml. per minute. The temperature of operation is 75° C. The extract obtained consists by weight of (total fatty acid ester basis) 2.3% methyl palmitate, 0.3% methyl stearate, 6.3% methyl oleate, 84.5% methyl linoleate, 6.5% methyl linolenate and 0.1% other. The raffinate obtained consists by weight of (total fatty acid ester basis) 51.9% methyl palmitate, 11.4% methyl stearate, 30.0% methyl oleate, 3.1% methyl linoleate, 2.8% methyl linolenate and 0.8% other. The extract product contains ester fraction which is about 91% pure polyunsaturates with a recovery in the extract of about 97% of the polyunsaturates from the feed.

The extract product from the first stage is stripped of solvent by conventional apparatus and vacuum distilled to remove impurities.

The raffinate from the first stage is stripped of solvent in preparation for the second stage.

In the second stage: the feed is the ester fraction obtained by stripping solvent from raffinate from the first stage. The solvent is ethyl acetate. The resin adsorbent is Amberlyst XN1010 (first batch) exchanged to 80% silver (valence state of 1) and 20% sodium; it has a particle size of through 20 and on 40 mesh (U.S. Sieve Series). The controller and valves of the demonstration unit are set so that the desorption zone includes two columns, the purification zone includes ten columns and the adsorption zone includes ten columns. The step time (the interval at which the flow pattern is advanced one column) is 6 minutes. The feed rate is 2.0 ml. per minute. The solvent introduction rate is 20.5 ml. per minute. The solvent to feed ratio is 10.3 to 1. The extract flow is 10.5 ml./minute. The raffinate flow is 12.0 ml. per minute. The temperature of operation is 75° C. The extract obtained consists by weight of (total fatty acid ester basis) 2.8% methyl palmitate, 0.3% methyl stearate, 77.3% methyl oleate, 10.5% methyl linoleate, and 9.1% methyl linolenate. The raffinate obtained consists by weight of (total fatty acid ester basis) 81.1% methyl palmitate, 15.8% methyl stearate, 1.5% methyl oleate, 0.1% methyl linoleate, 0.3% methyl linolenate and 1.2% other. The extract product contains ester fraction which is about 97% pure unsaturates with a recovery in the extract of about 95% of the unsaturates from the feed to the second stage.

The extract and raffinate products from the second stage are stripped of solvent by conventional means and vacuum distilled to remove impurities.

The above two-stage separation is readily carried out in simulated moving bed equipment with a buffer zone and recirculation loop with equal or better separation results with reduced solvent to feed ratios in each stage by appropriately adjusting process flow.

When a solvent consisting by volume of 50% hexane and 50% ethyl acetate is substituted in Example IV for the all ethyl acetate solvent used, similarly good separations are obtained when the resin used in the first stage is Amberlyst XN1010 having its exchangeable cation substituents consisting of 40% silver (valence state of one) substituents and 60% sodium (valence state of one) substituents and when the resin utilized in the second stage is Amberlyst XN1010 having its exchangeable cation substituents consisting of 70% silver (valence state of one) substituents and 30% sodium (valence state of one) substituents.

When a solvent consisting of acetone ($\delta=9.76$; $\delta_D=7.60$; $\delta_P=5.10$; and $\delta_H=3.40$) is substituted in Example IV for the all ethyl acetate solvent used, separations are obtained when the temperature of operation in each stage is about 50° C.

When a solvent consisting of methylene dichloride ($\delta=9.9$; $\delta_D=8.9$; $\delta_P=3.1$; and $\delta_H=3.0$) is substituted in Example IV for the all ethyl acetate solvent used, separations are obtained when the resin used in the first stage is Amberlyst XN1010 having its exchangeable cation substitutents consisting of 30% silver (valence state of one) substituents and 70% sodium (valence state of one) substituents and when the resin utilized in the second stage is Amberlyst XN1010 having its exchangeable cation substituents consisting of 60% silver (valence state of one) substituents and 40% sodium (valence state of one) substituents.

When a solvent consisting of diethyl ether ($\delta=7.65$; $\delta_D=7.1$; $\delta_P=1.4$; and $\delta_H=2.5$) is substituted in Example IV for the all ethyl acetate solvent used, similarly good separations are obtained when the resin used in the first stage is Amberlyst XN1010 having its exchangeable cation substituents consisting of 40% silver (valence state of one) substituents and 60% sodium (valence state of one) substituents and when the resin utilized in the second stage is Amberlyst XN1010 having its exchangeable cation substituents consisting of 70% silver (valence state of one) substituents and 30% sodium (valence state of one) substituents.

When a solvent consisting by volume of 10% methanol and 90% ethyl acetate (for this solvent blend: $\delta=9.29$; $\delta_D=7.67$; $\delta_P=2.94$; and $\delta_H=4.24$) is substituted in Example IV for the all ethyl acetate solvent used, similarly good separations are obtained when the resin used in the first stage is Amberlyst XN1010 having its exchangeable cation substituents consisting of 70% silver (valence state of one) substituents and 30% sodium (valence state of one) substituents and when the resin utilized in the second stage is Amberlyst XN1010 having its exchangeable cation substituents consisting of 90% silver (valence state of one) substituents and 10% sodium (valence state of one) substituents.

When in the above Examples I–IV, the resin adsorbent is derived from Amberlyst 15 or Amberlyst XN1005 or MSC-1 instead of from Amberlyst XN1010, similar separations are obtained.

While the foregoing describes certain preferred embodiments of the invention, modifications will be readily apparent to those skilled in the art. Thus, the scope of the invention is intended to be defined by the following claims.

What is claimed is:

1. A process for separating a fatty acid ester mixture according to degree of unsaturation, said process comprising the steps of
   (a) contacting a solution of said mixture in solvent with macroreticular strong acid cation exchange resin to selectively adsorb fatty acid ester of higher degree of unsaturation and to leave in solution in solvent a fraction of said mixture enriched in content of ester of lesser degree of unsaturation,
   (b) removing solution in solvent of fraction enriched in content of ester of lesser degree of unsaturation from contact with resin which has selectively absorbed fatty acid ester of higher degree of unsaturation,
   (c) contacting resin which has selectively absorbed fatty acid ester of higher degree of unsaturation with solvent to cause desorption of adsorbed ester and provide a solution in solvent of fraction enriched in content of ester of higher degree of unsaturation,
   (d) removing solution in solvent of fraction enriched in content of ester of higher degree of unsaturation from contact with resin;
the solvent in each step having the same composition and being characterized by a solubility parameter (on a 25° C. basis) ranging from about 7.0 to about 10.5, a solubility parameter dispersion component (on a 25° C. basis) ranging from about 7.0 to about 9.0, a solutility parameter polar component (on a 25° C. basis) ranging from about 0.2 to about 5.1 and a solubility parameter hydrogen bonding component (on a 25° C. basis) ranging from about 0.3 to about 7.4; said resin having its exchangeable cation substituents consisting essentially of from about 10% to about 90% heavy metal substituents and the remainder alkali metal and/or alkaline earth metal substituents; the solvent and the percentage of heavy metal substituents in the resin being selected to provide selectivity in step (a) and desorption in step (c).

2. A process as recited in claim 1, in which said solvent consists essentially by volume of from 0% to about 90% $C_5$–$C_{10}$ hydrocarbon and from 100% to about 10% carbonyl group containing compound selected from the group consisting of ester having the formula $$R-\overset{O}{\underset{\|}{C}}-O-CH_2-R_1$$

wherein R is hydrogen or alkyl chain containing one or two carbon atoms and $R_1$ is hydrogen or alkyl chain containing one to three carbon atoms and ketone having the formula

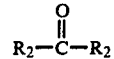

wherein each $R_2$ is the same or different and is alkyl chain containing 1 to 5 carbon atoms.

3. A process as recited in claim 2 in which said resin has its exchangeable cation substituents consisting essentially of from about 20% to about 85% heavy metal substituents and the remainder alkali metal and/or alkaline earth metal substituents.

4. A process as recited in claim 3, in which the heavy metal substituents are selected from the group consisting of silver, copper and gold, and in which the alkali metal and/or alkaline earth metal substituents are selected from the group consisting of sodium, potassium, barium, calcium and magnesium.

5. A process as recited in claim 4 in which said cation substituents are silver substituents in a valence state of one and sodium substituents.

6. A process as recited in claim 2, in which the solvent consists essentially of ethyl acetate.

7. A process as recited in claim 5, in which the solvent consists essentially of ethyl acetate.

8. A process as recited in claim 2, in which the solvent consists essentially by volume of from about 15% to about 60% hexane with the remainder being ethyl acetate.

9. A process as recited in claim 5 which is carried out by a continuous simulated moving bed technique.

10. A process as recited in claim 9, in which the fatty acid ester mixture is a mixture of methyl esters.

11. A process as recited in claim 1, in which the fatty acid ester mixture comprises a mixture of methyl ester of polyunsaturated fatty acid, methyl ester of monounsaturated fatty acid and methyl ester of saturated fatty acid and in which fatty acid ester of higher degree of unsaturation is methyl ester of polyunsaturated fatty acid.

12. A process as recited in claim 1, in which the fatty acid ester mixture comprises a mixture of methyl ester of monounsaturated fatty acid and methyl ester of saturated fatty acid and in which fatty acid ester of higher degree of unsaturation is methyl ester of monounsaturated fatty acid.

13. A process as recited in claim 1, in which the fatty acid ester mixture comprises a mixture of methyl ester of triunsaturated fatty acid and methyl ester of diunsaturated fatty acid and in which the fatty acid ester of higher degree of unsaturation is methyl ester of triunsaturated fatty acid.

14. A process as recited in claim 1, in which the solvent is characterized by a solubility parameter (on a 25° C. basis) ranging from about 7.5 to about 9.0, a solubility parameter dispersion component (on a 25° C. basis) ranging from about 7.25 to about 8.0, a solubility parameter polar component (on a 25° C. basis) ranging from about 1.0 to about 3.0 and a solubility parameter hydrogen bonding component (on a 25° C. basis) ranging from about 1.0 to about 4.0.

15. A solvent as recited in claim 1, in which the solvent consists by volume of from about 5% to about 35% $C_1$–$C_3$ alcohol and the remainder ethyl acetate.

* * * * *